United States Patent
Chattopadhyay et al.

(10) Patent No.: US 9,329,177 B2
(45) Date of Patent: May 3, 2016

(54) METHOD FOR MANUFACTURING AND USING A TEST PAPER AND CHEMICAL COMPOSITION THEREOF

(71) Applicant: National Yang Ming University, Taipei (TW)

(72) Inventors: Surojit Chattopadhyay, West Bengal (IN); Wei-Ju Liao, Taipei (TW)

(73) Assignee: National Yang Ming University, Taipei (TW)

( * ) Notice: Subject to any disclaimer, the term of this patent is extended or adjusted under 35 U.S.C. 154(b) by 195 days.

(21) Appl. No.: 13/943,541

(22) Filed: Jul. 16, 2013

(65) Prior Publication Data
US 2014/0356856 A1    Dec. 4, 2014

(30) Foreign Application Priority Data
May 29, 2013    (TW) .............................. 102118973 A

(51) Int. Cl.
*G01N 33/00*    (2006.01)
*G01N 33/543*    (2006.01)
*G01N 21/65*    (2006.01)

(52) U.S. Cl.
CPC .......... *G01N 33/54373* (2013.01); *G01N 21/65* (2013.01); *G01N 21/658* (2013.01); *G01N 2469/20* (2013.01)

(58) Field of Classification Search
CPC G01N 33/54373; G01N 21/658; G01N 21/65
See application file for complete search history.

(56) References Cited

U.S. PATENT DOCUMENTS

| | | | |
|---|---|---|---|
| 2004/0118317 A1* | 6/2004 | Iwai et al. | 106/1.23 |
| 2004/0135997 A1* | 7/2004 | Chan et al. | 356/301 |
| 2004/0146647 A1* | 7/2004 | Fixter et al. | 427/256 |
| 2004/0219348 A1* | 11/2004 | Jacquiod et al. | 428/304.4 |
| 2005/0006339 A1* | 1/2005 | Mardilovich et al. | 216/39 |
| 2005/0040535 A1* | 2/2005 | Kawata et al. | 257/765 |
| 2006/0147927 A1* | 7/2006 | Geddes | C12Q 1/6816 435/6.12 |
| 2007/0213410 A1* | 9/2007 | Hastwell et al. | 516/20 |

OTHER PUBLICATIONS

Song et al., Highly efficient synthesis of cyclic carbonates from CO2 and epoxides catalyzed by KI/lecithin, 2012, Catalysis Today, vol. 183, pp. 130-135.*

* cited by examiner

*Primary Examiner* — Melanie Y Brown
(74) *Attorney, Agent, or Firm* — Muncy, Geissler, Olds & Lowe, P.C.

(57) ABSTRACT

A method for manufacturing a test paper is disclosed in the present invention, and at least comprises the following steps. First, a chemical precursor comprising at least a reducing agent is coated onto a substrate. The substrate is then dipped into a metal salt solution comprising a plurality of metal ions for a predetermined time to reduce the metal ions to form metal particles on the substrate. Finally, the substrate is taken out and dried to complete a manufacture of at least a test paper. In the meantime a method for using the test paper, and a chemical composition used in the abovementioned for manufacturing the test paper are also disclosed in the present invention.

10 Claims, 7 Drawing Sheets

METHOD FOR MANUFACTURING AND USING A TEST PAPER AND CHEMICAL COMPOSITION THEREOF

CROSS-REFERENCE TO RELATED APPLICATIONS

This Non-provisional application claims priority under 35 U.S.C. §119(a) on Patent Application No(s). 102118973 filed in Taiwan, Republic of China, 05, 29, 2013, the entire contents of which are hereby incorporated by reference.

BACKGROUND OF THE INVENTION

1. Field of the Invention

This invention relates to a method for manufacturing a test paper and, more particularly, to a method for manufacturing a test paper, which is flexible, portable, high sensitive and can be extensively applied for the detection of pesticides used in fruit, drink contaminants, bio-molecular or regular chemical by utilizing an inkjet printing process, a method for using thereof and a chemical composition used in the abovementioned manufacturing method.

2. Description of the Related Art

Recently, "Food Safety" has become a serious issue in the life. Everyone questions whether the food and the drink we eat and drink everyday contains harmful or illegal additives. For example, melamine ($C_3H_3N_6$) will affect the urinary system and is not allowed above a certain 'country specific' limit. According to the FDA in US, Tolerable Daily Intake (TDI) of melamine is 0.63 mg/Kg per day. However, melamine is used as a food additive to fake an enhanced protein content in the food and thus the food with low protein content and quality can pass the test of the food inspection institute.

Therefore, a suitable analytical method is necessary in order to manage the food safety. Generally speaking, current analytical methods for testing prohibited substances are mainly HPLC-based that are time-consuming, expensive, and labor-intensive, requiring complex procedures of sample pre-treatment and well-trained technicians to operate them. In addition, low temperature fluorescence can also be used to inspect the abovementioned food with low quality. However, the sensing was mostly done on labeled molecules, which involves complexity and high precision techniques.

Raman spectrum, relies on inelastic scattering of light by vibrating molecules, and has been widely used to detect chemicals, such as diamond, medicine, and bio-molecule as well as the tool for studying molecules adsorbed on the surface. There are some advantages of Raman spectroscopy that the traditional clinical biochemical assay does not have. Further, Raman spectroscopy, different with other near-IR spectroscopy, is not greatly affected by water. Being a vibrational spectroscopy it suppresses the electronic transitions resulting in fluorescence. The technique will be very useful to apply on the detection of bio-molecules. However, Raman signals are quite weak which is restricted by the small Raman scattering cross section. In addition, as the concentration of general biomolecule is low, it is difficult to use Raman spectroscopy for bio detection.

It's worth noting that the application of Raman spectroscopy became more and more important due to the invention of Surface Enhanced Raman Scattering ("SERS" hereinafter). SERS signals arise from the molecules adsorbed on special rough metal surfaces that produces a huge enhancement (surface enhancement) of the previously weak Raman signal. Hence, this technique can detect very low concentrations of bio-samples or even single molecule because of the strongly enhanced signal. SERS offers a technique of observing and understanding the molecular structure and vibrational energy levels which are finger-prints for Raman active molecules. Basically, the single molecule detection techniques include fluorescence, near-field optics, far-field optics and evanescent wave. Compared to fluorescence method, SERS can obtain much more information of molecular vibration and can be applied on non-fluorescent molecules. Therefore, this technique not only can be widely used in bio-sensing, but also can be applied to ensure food safety.

Although various applications for SERS have been studied, but it is still limited by the choice of a simple and effective substrate and the roughness of the metal nanoparticles required for the surface enhancement. Moreover, the intensities of the Raman spectra and the orientation of the Raman active molecules are strongly correlated to result in larger errors and non-reproducible measurements qualitative analysis very difficult.

BRIEF SUMMARY OF THE INVENTION

According to the above, the present invention is to provide a method for manufacturing a test paper. The method disclosed herein is simple, and the manufactured test paper has advantages of being flexible, portable, and low cost and being able to be tuned with different concentrations of analyte.

Accordingly, the above method at least comprises the following steps. First, a chemical precursor comprising at least a reducing agent is coated onto a substrate. The substrate is then dipped into a metal salt solution comprising a plurality of metal ions for a predetermined time to reduce the metal ions to form metal particles on the substrate. Finally, the substrate is taken out and dried to complete a manufacture of at least a test paper.

In one embodiment of the invention, the chemical precursor may further comprise a catalyst. Before the step of coating the chemical precursor onto the substrate, the method further comprises a step of mixing the reducing agent and the catalyst to form the chemical precursor.

In one embodiment of the invention, the reducing agent can be a lecithin solution, and the concentration of the lecithin solution can vary from 25 mM to 75 mM.

In one embodiment of the invention, the catalyst can be a potassium iodide solution, and the concentration of the potassium iodide solution can vary from 10 mM to 100 mM.

In one embodiment of the invention, the metal salt solution is a hydrochloroauric acid solution, and the concentration of the aqueous solution of gold chloride can vary from 2 mM to 10 mM.

In one embodiment of the invention, the step of coating the chemical precursor onto the substrate further comprises the following steps. First, the chemical precursor is injected into a printer cartridge. And then, a scope and a pattern of coating the chemical precursor onto the substrate can be controlled by using a printer.

In one embodiment of the invention, the predetermined time is at least 2 hours.

In one embodiment of the invention, the substrate is a paper-related material.

In one embodiment of the invention, the metal particles are gold nanoparticles.

In one embodiment of the invention, the above method further comprises a step of coating an antibody layer to the surface of the test paper or performing a functional modification thereon.

Another aspect of the present invention is to provide a method for using the above test paper, and the method at least comprises the following steps. First, at least an analyte is coated onto the test paper. And then, a Raman signal is obtained from the test paper and the category of the analyte will be determined via the Raman signal. Preferably, the Raman signal is a surface enhanced Raman scattering signal.

Further aspect of the present invention is to provide a chemical composition used in the above method for manufacturing the test paper, and the chemical composition comprises a substrate, a reducing agent and a metal salt solution. Preferably, the substrate is a paper-related material, the reducing agent is a lecithin solution, and the metal salt solution is an aqueous solution of gold chloride.

Preferably, the chemical composition further comprises a coatable antibody.

The antibody can fix specific complementary molecules on the test paper for determination of their category by Surface enhanced Raman spectroscopy.

The features and advantages of the present invention will be understood and illustrated in the following specification and FIGS. 1-5B.

DETAILED DESCRIPTION OF THE INVENTION

Figure 1:
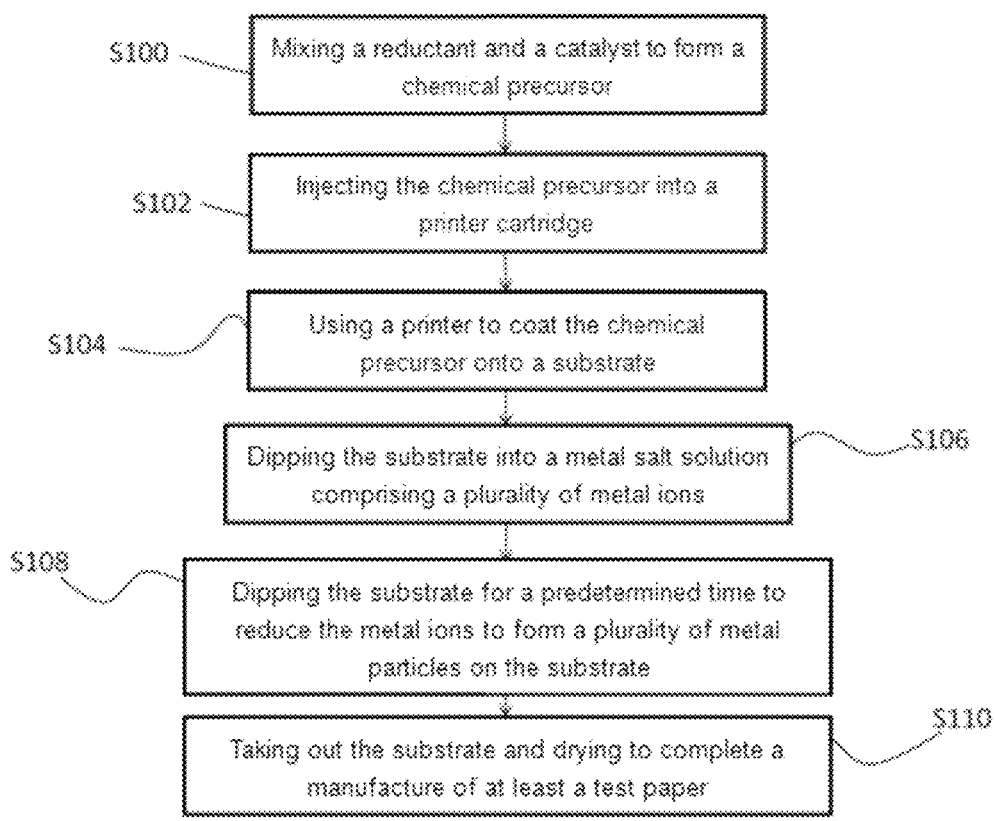
FIG. 1 is a flow chart showing a method for manufacturing a test paper according to an embodiment of the present invention.

According to the above, an aspect of the present invention is to provide a method for manufacturing a test paper, that is, it utilizes a simple and low cost process to provide the test paper which is flexible, portable and able to be tuned with different concentrations of analyte. Please refer to FIG. 1. FIG. 1 is a flow chart showing a method for manufacturing a test paper according to an embodiment of the present invention. First, a chemical precursor comprising at least a reducing agent is prepared. In a preferred embodiment of the present invention, the reducing agent is a lecithin solution, and the concentration of the lecithin solution can vary from 25 mM to 75 mM. In addition, the chemical precursor further comprises a catalyst, and preferably, the catalyst is a potassium iodide solution ("KI solution" hereinafter). It is needed to describe that the reducing agent used herein (namely lecithin) is a common component of human sweat. Thus, the whole process is a more safe and non-toxic process. Furthermore, the addition of the catalyst (namely KI) can be avoided easily that only affects the speed of the reduction and the present invention is not limited thereto.

Accordingly, as shown in step S100, 25 mM of the lecithin solution (also can be 50 mM or 75 mM) and 100 mM of the KI solution are mixed sufficiently with a ratio of 1:1 to form a chemical precursor by utilizing a stir bar at room temperature. And then, the chemical precursor is injected into a printer cartridge as shown in step S102.

Figure 2A:
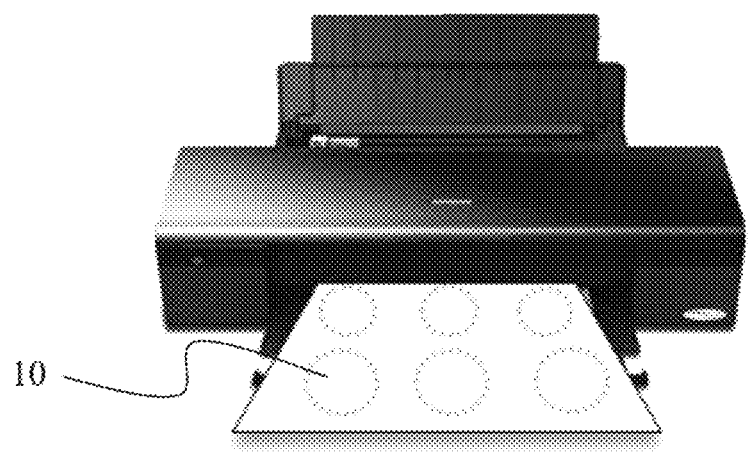
FIG. 2A to FIG. 2D are diagrams showing the operation from step S104 to step S108 according to the embodiment of the present invention.

Please simultaneously refer to FIG. 2A, FIG. 2A is a diagram showing the operation of step S104 according to the embodiment of the present invention. As shown in the figure, the chemical precursor is coated onto a substrate by using a printer after inserting the printer cartridge, which is injected with the chemical precursor, into the printer. Basically, it is noted that the chemical precursor is a bio-ink; therefore, the cleanness of the printer jet is needed to be check before inserting the printer cartridge filled with the bio-ink into the printer. Moreover, in the preferred embodiment, the printer is an ink-jet printer. Under the control of a computer, the printer can print a pattern with any shape and size on the substrate, that is, a plurality of patterns (namely the chemical precursor 10) on the substrate as shown in FIG. 2A. Preferably, the substrate is a paper-related material, but the present invention is not limited thereto.

Figure 2B:
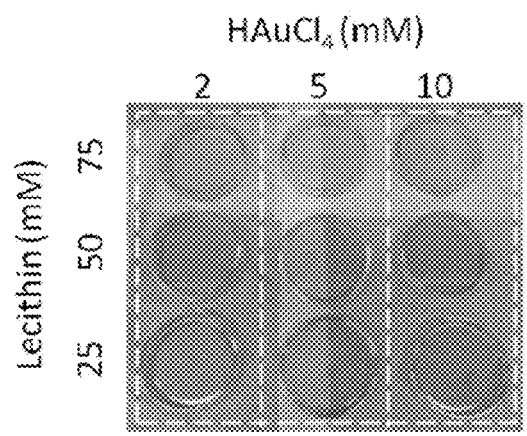

Please refer to FIG. 2B and step S106, FIG. 2B is a diagram showing the operation of step S106 according to the embodiment of the present invention. As shown in the figure, the patterns having the chemical precursor 10 are cut and dipped into culture dishes with 20 mL metal salt solution with different concentration (2 mM, 5 mM and 10 mM), separately, and the metal salt solution comprises a plurality of metal ions. In the preferred embodiment, the metal salt solution is a aqueous solution of gold chloride ($HAuCl_4 \cdot 3H_2O$).

Figure 2C:
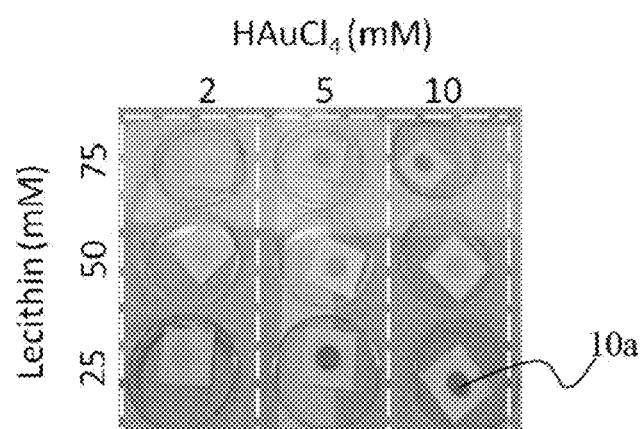

Please refer to FIG. 2C and step S108, FIG. 2C is a diagram showing the operation of step S108 according to the embodiment of the present invention. As shown in the figure, the metal ions will be gradually reduced to form a plurality of metal particles 10a on the substrate after dipping for a predetermined time. Accordingly, because the metal salt solution is preferably the aqueous solution of gold chloride, the metal ions are ionic gold ($Au^{3+}$), and the metal particles are gold nanoparticles. In details, because the printer generated patterns are formed by coating the chemical precursor comprising the reducing agent and the catalyst, a layer of metal particles will be formed in-situ on the pattern when the reducing agent reduces the metal ions of the metal salt solution. Therefore, the patterns of FIG. 2B will become purple as shown in FIG. 2C due to the formation of the gold nanoparticles. Basically, the lecithin solution used as the reducing agent can reduce partial ionic gold of the aqueous solution of gold chloride in few seconds under the existence of the KI solution used as the catalyst. However, it needs 2 hours to 24 hours to reduce all ionic gold of the aqueous solution of gold chloride, that is, the abovementioned predetermined time is at least 2 hours.

It is worthy to describe that the size and the arrangement of the gold nanopartcles are affected by the concentration of the aqueous solution of gold chloride, and the intensity of the following Raman signal is decided according to the size and the arrangement of the gold nanoparticles. That is, the size and the arrangement of the metal particles formed on the substrate can be changed by tuning the concentration of the aqueous solution of gold chloride for further changing the measuring range of the test paper manufactured in the following process.

Figure 2D:
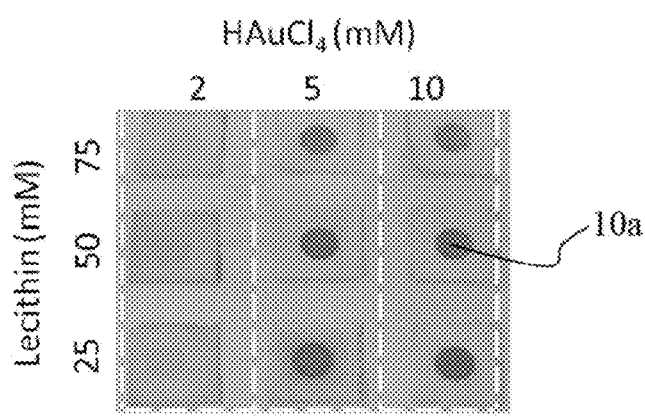
Figure 3:
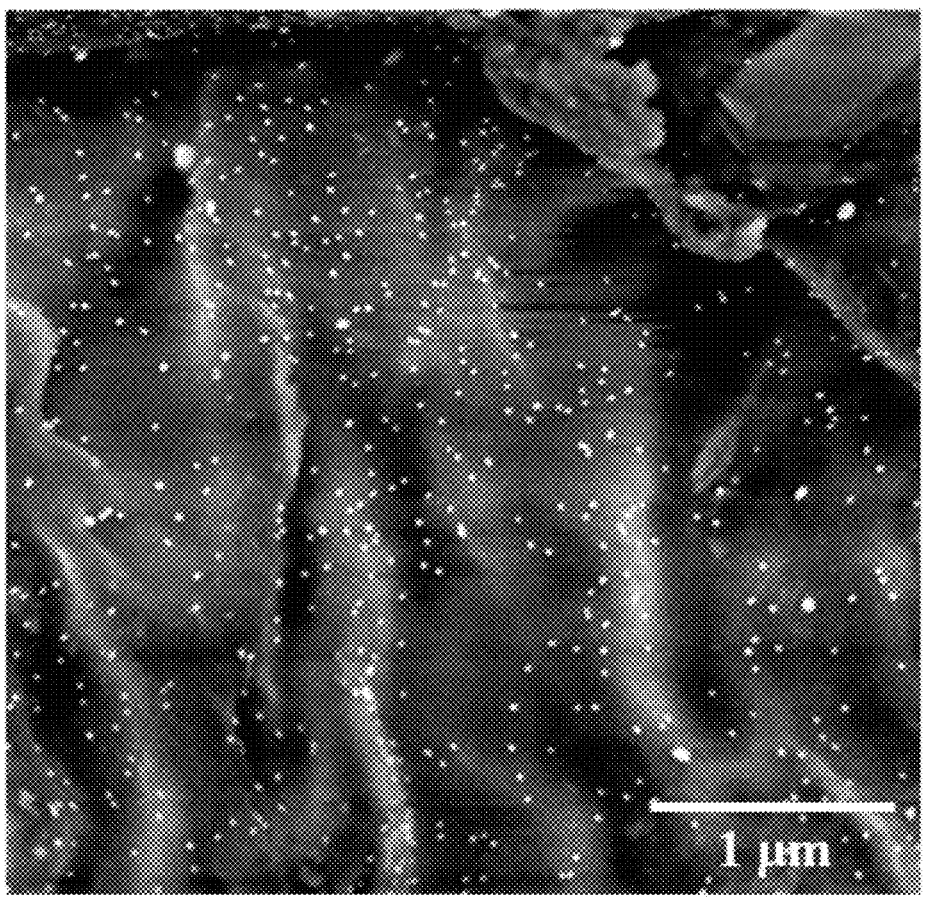
FIG. 3 is a SEM image showing the metal particles on the test paper according to the embodiment of the present invention.
Figure 4:
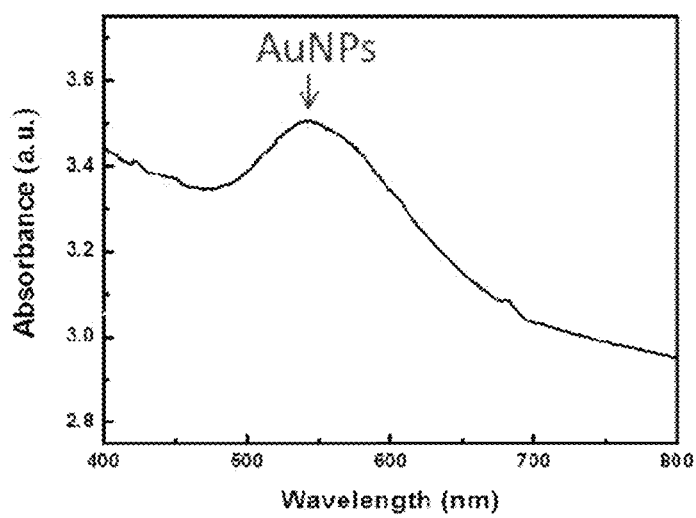
FIG. 4 is a UV-Vis spectrum showing the metal particles on the test paper according to the embodiment of the present invention.
Figure 5A:
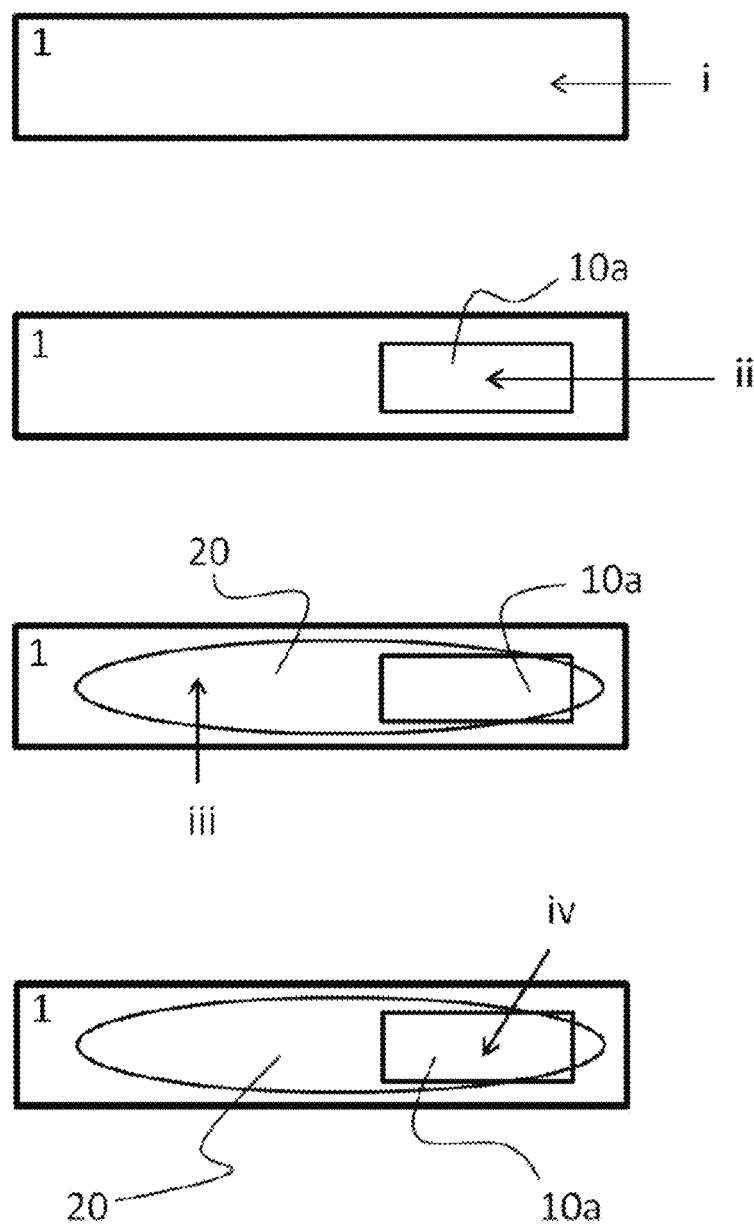
FIG. 5A is a diagram showing (i) a plain test paper, (ii) a test paper with a plurality of metal particles, (iii) a test paper with R6G, and (iv) a test paper with the metal particles containing R6G.
Figure 5B:
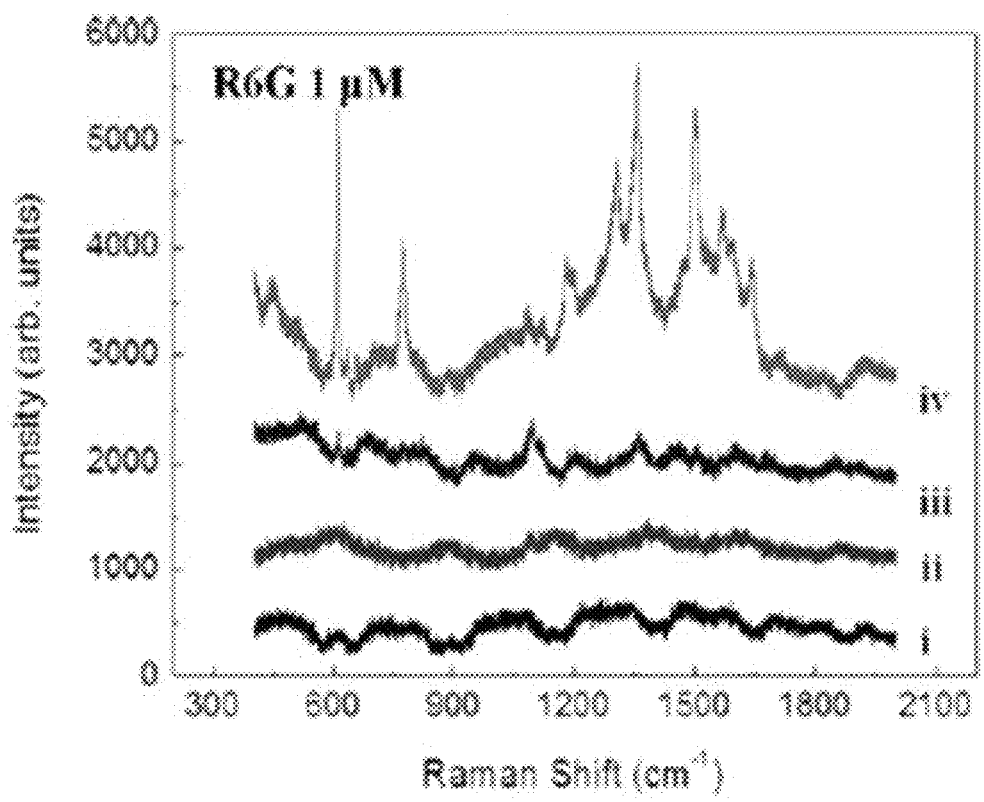
FIG. 5B is a diagram showing a Raman spectrum obtained from (i)~(iv) of FIG. 5A.

Please refer to step S100 and FIG. 2D, FIG. 2D is a diagram showing the operation of step S110 according to the embodiment of the present invention. After reducing all metal ions, the substrate is taken out and dried to complete the manufacturing process of the test paper.

Preferably, the surface of the test paper is coated with a antibody layer or performed by a functional modification for increasing the precision of detecting a specific antibody. In an embodiment, a scFv7 antibody layer is coated on the surface of the test paper, and the test paper is advantageous for H5N1 virus adhesion so that the existent amount of the H5N1 virus can be estimated.

In the meantime, the present invention provides a chemical composition used in the above manufacturing method, and the chemical composition at least comprises a substrate, a reducing agent and a metal salt solution. Preferably, the substrate is a paper-related material, the reducing agent is a lecithin solution, and the metal salt solution is an aqueous solution of gold chloride. Preferably, the chemical composition further comprises a coatable antibody.

After completing the manufacturing process, please refer to FIG. 3, FIG. 3 is a SEM image showing the metal particles on the test paper according to the embodiment of the present invention. The size of the gold nanoparticles formed on the substrate can vary from 20 nm to 30 nm.

Please refer to FIG. 4, it is needed to be further checked whether the metal particles formed on the test paper are gold nanoparticles or not. FIG. 4 is a UV-Vis spectrum showing the metal particles on the test paper according to the embodiment of the present invention, and its numerical curve fits in with the gold material (Au). Thus, the metal particles are gold nanoparticles true.

Another aspect of the present invention is to provide a method for using the abovementioned test paper, and the method at least comprises the following steps. First, an analyte is coated onto the test paper. A Raman signal is then obtained from the test paper, and the category of the analyte is determined via the Raman signal. Preferably, the Raman signal is a surface enhanced Raman scattering signal.

The methods for manufacturing and using the test paper are both described as above, and the effect of the test paper will be further illustrated as the following. Please refer to FIG. 5A and FIG. 5B. FIG. 5A is a diagram showing (i) a plain test paper, (ii) a test paper with a plurality of metal particles, (iii) a test paper with R6G; and (iv) a test paper with the metal particles containing R6G, and FIG. 5B is a diagram showing a Raman spectrum obtained from (i)~(iv) of FIG. 5A. As shown in FIG. 5A, a substrate 1 (namely a plain test paper) is used as a first comparative example in (i), and (ii) is to form a plurality of metal particles 10*a* on the substrate 1 as a second comparative example. The above two comparative examples can be used as background signals in the following detection. And then, the analyte 20 is coated on the substrate 1 having the metal particles 10*a*. At that time, one portion comprising the analyte 20 and the substrate 1 is detected as a first example (iii), and the other portion comprising the metal particles 10*a*, the analyte 20 and the substrate 1 is detected as a second example (iv).

In the preferred embodiment of the present invention, the concentration of the analyte is extremely low, that is, less than $10^{-10}$M (it is preferably $1\times10^{-16}$M). However, the present invention is not limited thereto. Moreover, an appropriate laser wavelength is chosen to achieve a strong enhanced effect. Preferably, Rhodamine 6G ("R6G" hereinafter) is used in the present invention. R6G is a standard molecule extensively used as a reference in Raman spextroscopy.

The Raman spectrums obtained from the positions of (i)~(iv) are shown in FIG. 5B. First, curve (iii) shows R6G signals at 612, 1363, and 1510 $cm^{-1}$. However, curve (iv) shows strong fingerprint signals of R6G, at 612, 774, 1363, and 1510 $cm^{-1}$. That is, compared with the traditional measuring method of Raman signal, the test paper provided in the present invention can enhance the contrast ratio of the Raman signal.

To sum up, the chemical precursor (bio-ink) can be easily coated onto the substrate through a single step according to the manufacturing method disclosed in the present invention. In addition, any complex pattern, that a printer can generate, can be transferred on to a test paper on which gold nanoparticles will grow in-situ. At that time, the test paper can be used with a portable Raman spectrometer to detect food safety and even toxic chemicals, on site, with high sensitivity and specificity, and thus time, cost and labor consumed in the measuring procedure will be greatly decreased.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A method for manufacturing a test paper, comprising:

printing a chemical precursor onto a substrate, wherein the chemical precursor is a mixture of a lecithin solution and a potassium iodide solution;

dipping the substrate into an aqueous solution of gold chloride for a predetermined time to form a plurality of gold nanoparticles on the substrate; and taking out the substrate, and drying to complete a manufacture of at least a test paper.

2. The method according to claim 1, wherein the concentration of the lecithin solution varies from 25 mM to 75 mM.

3. The method according to claim 1, wherein the concentration of the potassium iodide solution varies from 10 mM to 100 mM.

4. The method according to claim 1, wherein the concentration of the aqueous solution of gold chloride varies from 2 mM to 10 mM.

5. The method according to claim 1, wherein the step of printing the chemical precursor onto the substrate further comprises:

injecting the chemical precursor into a printer cartridge; and using a printer to control a scope and a pattern of printing the chemical precursor onto the substrate.

6. The method according to claim 1, wherein the predetermined time is at least 2 hours.

7. The method according to claim 1, wherein the substrate is a paper-related material.

8. The method according to claim 1, further comprising:

coating an antibody layer or performing a functional modification to the surface of the test paper.

9. A method for determining an analyte category comprising:

coating printing a chemical precursor onto a substrate, wherein the chemical precursor at least comprises a reducing agent is a mixture of a lecithin solution and a potassium iodide solution;

dipping the substrate into a metal salt solution including a plurality of metal ions;

dipping the substrate into an aqueous solution of gold chloride for a predetermined time to reduce the metal ions to form a plurality of metal particles gold nanoparticles on and in the substrate;

taking out the substrate, and drying to complete a manufacture of at least a test paper;

coating at least an analyte onto the test paper;

obtaining a Raman signal from the test paper; and determining the category of the analyte via the Raman signal.

10. The method according to claim 9, wherein the Raman signal is a surface enhanced Raman scattering signal.

* * * * *